United States Patent [19]

Nonaka et al.

[11] Patent Number: 5,055,310

[45] Date of Patent: Oct. 8, 1991

[54] PROCESS OF PREPARING SHELF-STABLE "TOFU" AT NORMAL TEMPERATURE FOR LONG TERM

[75] Inventors: Masahiko Nonaka; Takahiko Soeda; Keiko Yamagiwa; Hiroko Kowata; Masao Motogi; Seiichiro Toiguchi, all of Kawasaki, Japan

[73] Assignee: Ajinomoto Co., Inc., Tokyo, Japan

[21] Appl. No.: 401,831

[22] Filed: Sep. 1, 1989

[30] Foreign Application Priority Data

Sep. 2, 1988 [JP] Japan .................................. 63-219703

[51] Int. Cl.$^5$ ............................................. A23L 1/20
[52] U.S. Cl. ........................................ 426/46; 426/52; 426/61; 426/573; 426/634
[58] Field of Search ....................... 426/46, 52, 61, 63, 426/573, 634, 392, 521

[56] References Cited

FOREIGN PATENT DOCUMENTS 0244152 11/1987 European Pat. Off. .............. 426/46
0059151 4/1984 Japan ..................................... 426/46

Primary Examiner—Marianne Cintins
Attorney, Agent, or Firm—Oblon, Spivak, McClelland, Maier & Neustadt

[57] ABSTRACT

Shelf stable soybean curd which is stable for extended periods of time is prepared by reacting soy milk with a solidifying agent and a transglutaminase, which is not dependent on $Ca^{+2}$ ions and which is capable of catalyzing the acyl rearrangement of $\gamma$-carboxyamide in the glutamine residue of a peptide chain at a temperature not higher than 80° C. to prepare a soybean curd, packing the thus prepared soybean curd in a heat-resistant container, and retorting the packaged soybean curd.

7 Claims, 2 Drawing Sheets

PROCESS OF PREPARING SHELF-STABLE "TOFU" AT NORMAL TEMPERATURE FOR LONG TERM

BACKGROUND OF THE INVENTION

1. Field of the Invention

The present invention relates to a method of preparing retort "TOFU" or soybean curd.

2. Description of the Background

In order to keep soybean curd over long periods of time, the curd is stored in sterile packages and the like. However, this method requires a special environment for preparation of the stored curd. The method is basically a chilled storage technique, but is not satisfactory over long terms of storage.

One method which has recently been developed for improving the stability of soybean curd involves imparting freezing resistance to soybean curd (Japanese Patent Publication No. 31942/1981). The stability of the curd indeed is improved by this technique, but it is impossible to store soybean curd over time periods longer than 6 months. A need therefore exists for an improved technique of storing soybean curd over extended periods of time.

SUMMARY OF THE INVENTION

Accordingly, one object of the present invention is to provide a method of preparing soybean curd which exhibits improved stability upon long term storage.

Briefly, this object and other objects of the present invention as hereinafter will become more readily apparent can be attained in a process for preparing shelf stable soybean curd which is stable for extended periods of time by reacting soy milk with a solidifying agent and a transglutaminase, which is not dependent on $Ca^{+2}$ ions and which is capable of catalyzing the acyl rearrangement of γ-carboxamide in the glutamine residue of a peptide chain at a temperature not higher than 80° C. to prepare a soybean curd; packing the thus prepared soybean curd in a heat-resistant container; and retorting the packaged soybean curd.

DETAILED DESCRIPTION OF THE PREFERRED EMBODIMENTS

Figure 1:
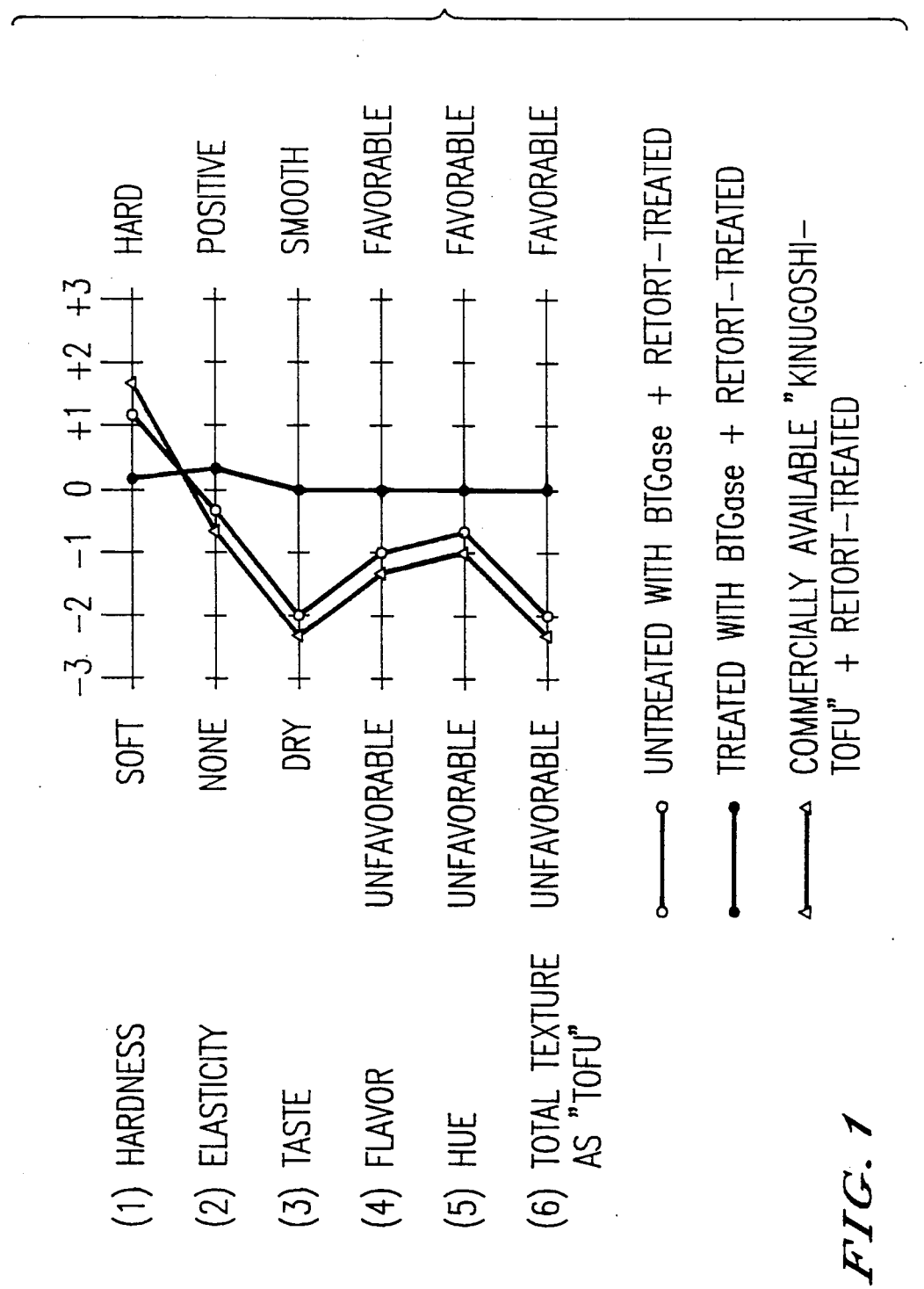
Figure 2:
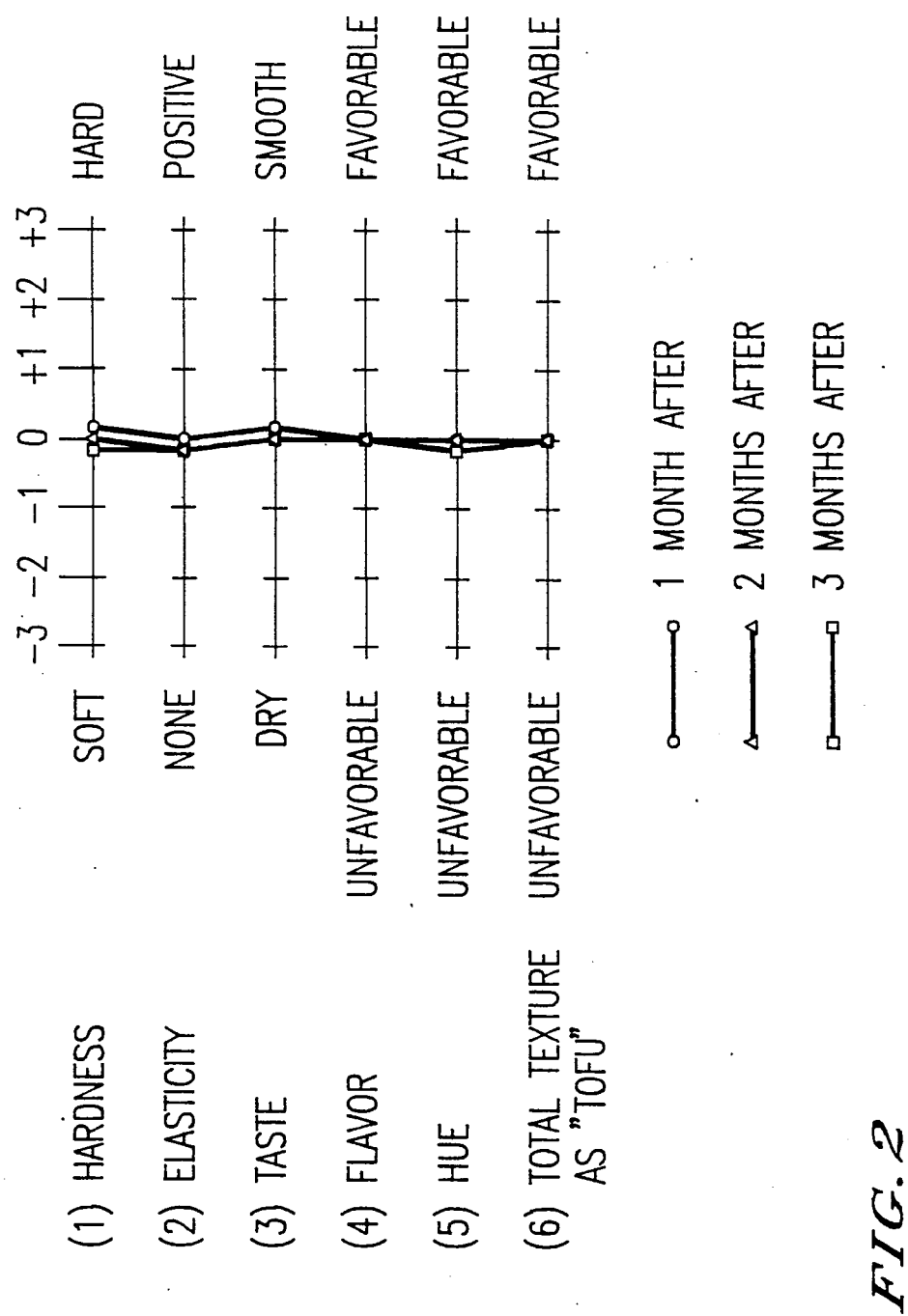

As a result of extensive investigations, it has now been found that when a soy milk is reacted with a solidifying agent to prepare soybean curd, retort resistance can be imparted to soybean curd by reacting soy milk with transglutaminase (hereinafter sometimes simply referred to as BTGase), which is non-dependent on $Ca^{2+}$ and which is capable of catalyzing the acyl requirement of γ-carboxyamide in the glutamine residue of peptide chains, together with a solidifying agent, and then the thus prepared soybean curd is packaged in a heat resistant container and subjected to a retort treatment to prepare retorted soybean curd. BTGase is a recently discovered enzyme and is disclosed and claimed in Japanese Patent Application No. 165067/1987 in which some of the present inventors participated. Its enzymatic characteristics, process for production, and the like are described hereinafter.

According to the present invention, a soybean curd is provided which has retort resistance and which can be circulated at normal temperature over long periods of time for 6 months or longer.

In order to prepare a soybean curd which is storable at ambient temperatures over long periods of time, a solidifying agent and BTGase are reacted with soy milk to prepare a soybean curd. The curd is then packed in a heat-resistant container such a retort pouch, or the like. The preparation is carried out by the usual process of preparing a soybean curd except that BTGase is used in combination with the solidifying agent. Some restrictions are imposed on the process as a consequence of the combined use of these ingredients.

Various methods can be employed for preparing soy milk which is useful in the present invention. A first method is the preparation of soy milk from whole soybeans. Such a soy milk can be obtained by impregnating whole beans with water preferably at a water temperature of 5° to 30° C. for 8 to 24 hours, grinding the beans, adding water until the water content desirably is 7 to 8 times the water content of raw soybean, including the water absorbed in the impregnation step, adding a defoaming agent which includes various edible defoaming agents such as fatty acid monoglycerides, silicone resins and the like, heating and steaming the beans, whereby protein and fats are efficiently extracted into the soy milk and at the same time, the temperature is elevated to, e.g., 100° C. over 5 minutes and the system is then kept at the temperature for 3 to 5 minutes using various apparatuses for sterilization and inactivation of inhibitors and finally squeezing the solid material to separate and remove "OKARA" or bean curd lees.

A second method of preparing soy milk involves the preparation of the milk from whole fat soy milk powders. The milk is obtained by adding water to soy milk powders in a 7 to 15-fold amount, preferably 9 to 11-fold amount, heating with stirring to a temperature elevated to about 100° C. over 2 to 10 minutes at which temperature the system is kept for 2 to 10 minutes and then allowing the milk to cool.

A third method is a soy milk obtained from a soybean protein isolate. In this method water, oils and fats such as vegetable oils, and the like and, if necessary, further starch, are added to defatted protein powders having a protein content of, e.g., 50% or more along with various emulsifying agents. This matter is heated to emulsify the ingredients in the water medium.

In a conventional process for preparing soybean curd, soybean curd having a desired hardness is prepared by adding solidifying agents such as various calcium sulfate hydrates, calcium chloride, natural NIGARI or brine, glucono-δ-lactone (GDL), or the like to soy milk solutions in a concentration of 0.1 to 5%, stirring, allowing the soy milk to stand, solidifying the soy milk solution, and dehydrating the solution to an appropriate extent. According to the present invention, BTGase acts together with the solidifying agent in the solidifying treatment.

The purpose of using BTGase in combination with the solidifying agent is to activate the ability of protein to crosslink so that it is converted into high molecular weight molecules and to prepare soybean curd having retort resistance. For this purpose, the following conditions for solidification may be employed.

i) Concentration of protein in soy milk: 3–10% preferably 4–7%.

ii) Solidifying agent: all agents used generally for preparation of soybean curd, preferably GDL.

iii) Concentration of BTGase: 0.1–100 U/g protein, preferably 1–10 U/g protein.

iv) Temperature for solidification: 80° C. or lower, preferably 50°–70° C.

v) Time for solidification: 10 minutes to overnight, preferably 30 to 120 minutes.

Needless to say, various additives such as emulsifying agents, and the like conventionally used in the preparation of soybean curd may also be added in the preparation step in such a range that does not inhibit the effects of the present invention.

After the solidification step, the solidifying liquid is filtered and dehydrated to prepare soybean curd having a desired hardness. Alternatively, the solidifying liquid is allowed to stand, cooled or incubated to prepare soybean curd. In any case, the solidifying liquid obtained by the solidification treatment may also be treated in a conventional manner. The solution may be incubated advantageously at 5° to 60° C. for 1 to 24 hours. By performing the operation, the soybean curd is kept better shape and the water retention ability of the curd is further improved.

Next, the thus prepared soybean curd is packed in a heat-resistant container such as a retort pouch, or the like, which is then retorted to form the final product. The thus prepared soybean curd has a retort resistance. Conditions for heating in the retorting step may be set at 80° to 130° C., preferably 100° to 125° C., for 5 to 120 minutes, preferably 10 to 30 minutes. There are no other particular restrictions involved for obtaining the final product. However, the actual retorting step is controlled by the $F_0$ value and is performed at an $F_0$ value within the range of from 0.2 to 6, preferably 2 to 4. The term $F_0$ value refers to the minimum heating time (minutes, seconds) required for killing a definite number of microorganisms at a definite temperature and generally means the minimum lethal heating time ($F_0$) at 250° F. (121.1° C.). This value is used to provide an index which represents a sterilizing effect on food with heating.

The reason why such conditions for the retorting step is to ensure storage at normal temperature over periods of longer than 6 months with quality under hygenic conditions.

Accordingly, the thus prepared retorted soybean curd can be circulated at normal temperature over long periods of time for 6 months or longer.

The transglutaminase BTGase employed in the present invention.

(1) Transglutaminase and its origin

Transglutaminase (TGase) is an enzyme which catalyzes the acyl rearrangement of γ-carboxyamide group of the glutamine moiety present in a peptide chain. When this TGase acts on the ε-amino group in the lysine moiety of a protein as an acyl receptor, an ε-(γ-Glu)-Lys crosslinking linkage is formed. Further when water functions as the acyl receptor, TGase promotes the reaction wherein the glutamine residue is deamidated and converted into a glutamic acid residue.

Utilizing the properties of TGase, a protein-containing solution or slurry can be gelled using this enzyme.

TGase of animal origin such as the TGase derived from the liver of a guinea pig (MTGase) is known. However, it is difficult to obtain TGase of animal origin at low cost in large quantities. In addition, for the gelation of protein, it is necessary to increase both the enzyme concentration and substrate concentration. Furthermore, TGase of animal origin is $Ca^{2+}$-dependent so that its application is limited.

The transglutaminase (BTGase) used in the present invention is produced by microorganisms, for example, bacteria belonging to the genus Streptoverticillium, but there is no report thus far which describes a TGase derived from a microorganism.

The BTGase derived from microorganisms used in the present invention is available at low cost and can be purified in a simple way so that it is a practically useful enzyme. In addition, the use of BTGase provides advantages in that gelled products having excellent quality can be prepared both in the absence of calcium and in the presence of calcium, at very low concentrations of enzyme (BTGase) and substrate.

(2) Production of BTGase

Suitable BTGase producing microorganisms include *Streptoverticillium griseocarneum* IFO 12776, *Streptoverticillium cinnamoneum* sub s. *cinnamoneum* IFO 12852, *Streptoverticillium mobaraense* IFO 13819, and the like.

Procedures for culturing and purifying these microorganisms and collecting transglutaminase are as follows.

In order to incubate the microorganism any liquid culture or solid culture can be performed. From an industrial viewpoint, however, it is advantageous to use an aerobic deep spinner culture. Further, in the culturing step, carbon sources, nitrogen sources, inorganic salts and other trace nutrient sources, and the like, which are normally used for the culturing of microorganisms, can be used, and other nutrient sources utilizable with microorganisms belonging to the genus Streptoverticillium are all usable. Suitable carbon sources for the medium include glucose, sucrose, rastagen, glycerin, dextrin, starch and the like, as well as fatty acids, oils and fats, organic acids, and the like, singly or in combination. Suitable nitrogen sources include any inorganic nitrogen source or organic nitrogen source. Suitable inorganic nitrogen sources include ammonium nitrate, ammonium sulfate, urea, sodium nitrate, ammonium chloride, and the like. Suitable organic nitrogen sources include powders of soybean, rice, sweet corn, wheat and the like; sugars, defatted lees, and the like, and also corn steep liquor, pentone, meat extract, casein, amino acids, yeast extract, and the like. Suitable inorganic salts and trace nutrient sources include salts of phosphoric acid, magnesium, potassium, iron, calcium, zinc and the like. In addition, vitamins, nonionic surface active agents, defoaming agents, and the like which can accelerate the growth of the bacteria or production of BTGase can be used, depending upon necessity.

Culturing is performed under aerobic conditions at such a temperature range that bacteria grow and BTGase is produced, preferably at 25° to 35° C. The time period for incubation varies depending upon the conditions, but the incubation is normally conducted until the maximum amount of BTGase is produced. The time period is generally about 2 to about 4 days.

BTGase is dissolved in the culture solution in liquid culture and collected from the culture filtrate after the solid content is removed from the culture solution after completion of culturing.

To purify BTGase from the culture filtrate, any method generally used for the purification of enzyme can be used. For example, a treatment with an organic solvent such as ethanol, acetone, isopropyl alcohol, or the like; salting-out with ammonium sulfate, sodium chloride, or the like; dialysis, ultrafiltration, ion exchange chromatography, adsorption chromatograhy, gel filtration, adsorbents, isoelectric point fractionation, and the like can be used. Further when the purity of the BTGase is desired to be further increased, this can be done by appropriate combinations of these methods.

According to these methods, the liquid or solid BTGase can be obtained by ultrafiltration concentration, reverse osmosis concentration, drying under reduced pressure, freeze drying, spray drying, or the like by adding or without adding various salts, sugars, proteins, fats, surface active agents, and the like as stabilizers.

The activity of BTGase can be determined as follows. A reaction is carried out in the absence of $Ca^{2+}$ using benzyloxycarbonyl-L-glutaminylglycine or hydroxylamine as a substrate. The hydroxamic acid which forms is treated with trichloroacetic acid and an iron complex is formed, and the amount of complex formed is determined by adsorption at 525 nm. The amount of hydroxamic acid is determined by comparison to a calibration curve and the activity is calculated.

BTGase activity can be determined by the method described below, unless otherwise indicated.

| | |
|---|---|
| Reagent A: | 0.2 M Tris-hydrochloride buffer (pH 6.0) |
| | 0.1 M hydroxylamine |
| | 0.01 M reductive glutathione |
| | 0.03 M benzyloxycarbonyl-L-glutaminylglycine* |
| | Reagent A is 0.2 M Tris-hydrochloride buffer (pH 6.0) containing 0.1 M hydrorylamine, 0.01 M reductive glutathione and 0.03 M benzyloxycarbonyl-L-glutaminylglycine. |
| Reagent B: | 3N hydrochloric acid |
| | 12% trichloroacetic acid |
| | 5% $FeCl_3.6H_2O$ (soluble in 0.1 N HCl) |

The *1:1:1 mixture of the above solutions is made reagent B. This ratio is volume percent.*

Reagent A, 0.5 ml, is added to and mixed with 0.05 ml of enzyme solution. After reaction at 37° C. for 10 minutes, reagent B is added to the reaction mixture to terminate the reaction and to form an Fe complex. Then, the absorbancy is measured at 525 nm. For a control, a solution of enzyme which was previously inactivated by heating is similarly reacted and its absorbance is measured to determine its difference in absorbance from the enzyme solution. Separately, a calibration curve is prepared using L-glutamic acid γ-monohydroxamic acid instead of the enzyme solution. Based on the difference in absorbance, the amount of hydroxamic acid which forms is determined. An enzyme activity that produces 1 μmole of hydroxamic acid for one minute is defined as one unit.

(3) Enzyme properties of BTGase

The enzymological properties of the thus obtained purified BTGase, that is, the transglutaminase of *Streptoverticillium mobaraense* IFO 13819 (named BTG-1), transglutaminase of *Streptoverticillium griseocarneum* IFO 12776 (named BTG-2) and transglutaminase of *Streptoverticillium cinnamoneum* sub s. *cinnamoneum* IFO 12852 (named BTG-3) are as follows.

a) Optimum pH

When benzyloxycarbonyl-L-glutaminylglycine and hydroxylamine are used as substrates, the optimum pH values of BTG-1, BTG-2 and BTG-3 are each at about 6 to 7.

b) Optimum temperature

When benzoyloxycarbonyl-L-glutaminylglycine and hydroxylamine are used as substrates, the optimum temperatures of BTG-1, BTG-2 and BTG-3 are at about 55° C., about 45° C. and about 45° C., respectively, when reacted at pH 6 for 10 minutes.

c) pH stability

When treated at 37° C. for 10 minutes, BTG-1, BTG-2 and BTG-3 are stable at a pH of from 5 to 9, a pH of from 5 to 9 and a pH of from 6 to 9, respectively.

d) Temperature stability

When treated at pH 7 for 10 minutes, BTG-1 retains 80% of its activity at 40° C. and 74% at 50° C.; BTG-2 retains 86% of its activity at 40° C. and 56% at 50° C.; and BTG-3 retains 80% of its activity at 40° C. and 53% at 50° C.

e) Substrate specificity

Using each BTGase, the reactivity of the same with various synthetic substrates were benzyloxycarbonylasparaginylglycine, benzyloxycarbonylglutamine and glycyl-glutaminylglycine. When the synthetic substrate was benzyloxycarbonylglutaminylglycine, the reactivity is the highest. In this determination, the concentration of the various synthetic substrates was set at 5 mM. The results are shown in Table 1.

In Table 1, CBz, Gln, Gly and Asp are the abbreviations for the benzyloxycarbonyl group, the glutamyl group, the glycyl group and the asparaginyl group, respectively.

TABLE 1

| Substrate | BTG-1 (%) | BTG-2 (%) | BTG-3 (%) |
|---|---|---|---|
| CBz—Gln—Gly | 100 | 100 | 100 |
| CBz—Gin—Gly—OEt | 63 | 44 | 42 |
| CBz—Gln—Gln—Gly | 38 | 39 | 35 |
| CBz—Gly—Gln—Gly—Gly | 8 | 12 | 11 |
| CBz—Gly—Gly—Gln—Gly | 23 | 58 | 60 |
| CBz—Gln | 0 | 0 | 0 |
| CBz—Asp—Gly | 0 | 0 | 0 |
| Gly—Gln—Gly | 0 | 0 | 0 | f) Influence of metal ions

The influence of metal ions was determined by adding various metal ions to the activity assay system in a concentration of 1 mM. The results are shown in Table 2. For any of the BTGase(s), the activity is inhibited by $Cu^{2+}$ and $Zn^{2+}$.

TABLE 2

| Metal Ions | BTG-1 (%) | BTG-2 (%) | BTG-3 (%) |
|---|---|---|---|
| None | 100 | 100 | 100 |
| $CaCl_2$ | 101 | 102 | 102 |
| $BaCl_2$ | 101 | 99 | 105 |
| $CoCl_2$ | 103 | 103 | 103 |
| $CuCl_2$ | 79 | 82 | 86 |
| $FeCl_2$ | 96 | 104 | 106 |
| KCl | 96 | 99 | 105 |
| $MgCl_2$ | 102 | 104 | 103 |
| $MnCl_2$ | 98 | 97 | 97 |
| NaCl | 99 | 102 | 101 |
| $NiCl_2$ | 102 | 100 | 101 |
| $Pb(CH_3COO)_2$ | 97 | 97 | 100 |
| $SrCl_2$ | 100 | 101 | 100 |
| $ZnCl_2$ | 15 | 24 | 24 | g) Influence of inhibitor

Each inhibitor was added to the assay system in a concentration of 1 mM. After allowing the assay medium to stand at 25° C. for 30 minutes, the activity was determined. The results are shown in Table 3. For any of the BTGase(s), the activity is inhibited by p-chloromercurybenzoic acid (PCMB), N-ethylmaleimide (NEM) and monoiodoacetic acid.

TABLE 3

| Inhibitor | BTG-1 (%) | BTG-2 (%) | BTG-3 (%) |
|---|---|---|---|
| None | 100 | 100 | 100 |

TABLE 3-continued

| Inhibitor | BTG-1 (%) | BTG-2 (%) | BTG-3 (%) |
|---|---|---|---|
| EDTA | 102 | 98 | 99 |
| PCMB | 54 | 61 | 63 |
| NEM | 5 | 5 | 5 |
| Monoiodoacetic acid | 64 | 50 | 67 |
| PMSF | 104 | 95 | 101 |

In Table 3, PMSF is the abbreviation for phenylmethylsulfonylfluoride.

h) Isoelectric point

The isoelectric point for each enzyme was determined by Ampholine isoelectric point electrophoresis. BTG-1, BTG-2 and BTG-3 have isoelectric points pI at about 9, at about 9.7 and at about 9.8, respectively.

i) Molecular weight

Molecular weight was determined by SDS disc electrophoresis molecular weights of BTG-1, BTG-2 and BTG-3 are about 38,000, about 41,000 and about 41,000, respectively.

j) Comparison with MTGase

The properties of BTGase are compared to those of the transglutaminase of guinea pig liver (MTGase). MTGase was prepared by the method described in Japanese Patent Application Laid-Open No. 58-149645.

Table 4 shows the comparison of the enzymological properties of the BTG-1 to BTG-3 enzymes. Table 5 shows the influence of $Ca^{2+}$ ions on activity. As is clear from Tables 4 and 5, various differences in enzymological properties are noted between MTGase, primarily studied in the past, and Streptomyces-derived BTGase. Differences are noted particularly in temperature stability, molecular weight, isoelectric point and substrate specificity. In addition, a clear difference in the activity site of BTGase employed in the present invention is observed in the presence of and in the absence of $Ca^{2+}$. Accordingly, it is believed that each enzyme of the present invention is different from MTGase, as can be ascertained from the property differences.

TABLE 4

|  | BTG-1 | BTG-2 | BTG-3 | MTGase |
|---|---|---|---|---|
| Optimum pH | 6-7 | 6-7 | 6-7 | 6 |
| pH stability | 5-9 | 5-9 | 6-9 | 6-7.5 |
| Optimum temperature | ca 55° C. | ca. 45° C. | ca. 45° C. | 50-55° C. |
| Temperature stability (%) | | | | |
| 40° C. residual rate | 88 | 86 | 80 | 96 |
| 50° C. residual rate | 74 | 56 | 53 | 40 |
| Molecular weight | ca. 38,000 | ca. 41,000 | ca. 41,000 | ca. 90,000 |
| Isoelectric point | 9.8 | 9.7 | 9.8 | 4.5 |
| Substrate specificity (%): | | | | |
| CBz—Gln—Gly | 100 | 100 | 100 | 100 |
| CBz—Gln—Gly—OEt | 63 | 44 | 42 | 122 |
| CBz—Gln—Gln—Gly | 38 | 39 | 35 | 288 |
| CBz—Gly—Gln—Gly—Gly | 8 | 12 | 11 | 126 |
| CBz—Gly—Gly—Gln—Gly | 23 | 58 | 60 | 27 |

TABLE 5

| Metal Ion | BTG-1 (%) | BTG-2 (%) | BTG-3 (%) | MTGase (%) |
|---|---|---|---|---|
| None | 99 | 98 | 100 | 0 |
| 1 mM $CaCl_2$ | 100 | 100 | 99 | 39 |
| 5 mM $CaCl_2$ | 100 | 100 | 98 | 100 |

(4) Preparation Example of BTGase a) Preparation of BTG-1

A 200 ml of medium (pH 7) having a composition of: 0.2% polypeptone, 0.5% of glucose, 0.2% of dipotassium phosphate and 0.1% of magnesium sulfate was inoculated with Streptoverticillium mobaraense IFO 13819 followed by culturing at 30° C. for 48 hours. The obtained seed culture solution was added to 20 liters of a medium (pH 7) composed of 2.0% of polypeptone, 2.0% of rastagen, 0.2% of dipotassium phosphate, 0.1% of magnesium sulfate, 0.2% of yeast extract and 0.05% of ADEKANOL (trademark, manufactured by Asahi Denka Kogyo K.K.) as a defoaming agent. After culturing at 30° C. for 3 days, the medium was filtered thereby giving 18.5 liters of the culture solution. The activity was 0.35 U/ml.

The pH of the culture solution was adjusted to 6.5 with hydrochloric acid. The culture solution was passed through a column of CG-50 (trademark, manufactured by Organo Inc.), which had been previously equilibrated with 0.05M phosphate buffer (pH 6.5). By this operation, transglutaminase was adsorbed. After protein impurities were further washed out with the same buffer, a 0.05 to 0.5M density gradient of the same buffer was prepared and the buffer was passed through the column. The eluate was fractionated and recovered. Fractions showing high specific activity were collected. After the fractions were diluted so as to show a conductivity of 10 ms or less, the dilution was passed through a column of blue Sepharose. By this operation, transglutaminase was adsorbed. After impurities were further washed out with 0.05M phosphate buffer (pH 7), a 0 to 1M density gradient of sodium chloride was prepared. By passing the liquid through the column, the eluate was recovered. Fractions showing high specific activity were collected. The fractions were concentrated using a UF 6000 membrane and equilibrated with 0.05M phosphate buffer (pH 7) containing 0.5M sodium chloride.

The resulting concentrate was passed through a Sephadex G-75 column (manufactured by Pharmacia Fine Chemicals, Inc.), which had previously been equilibrated with the same buffer. The buffer was passed through the column and the eluate was obtained as fractions. As the result, the active fraction was eluted as a single peak. The specific activity of the fraction was 625 times that of the culture filtrate and the recovery rate was 47%.

b) Preparation of BTG-2

After *Streptoverticillium griseocarneum* IFO 12776 was cultured at 30° C. for 3 days in the same manner as in the case of BTG-1, the system was filtered to give 19 liters of culture solution. The activity was 0.28 U/ml.

The enzyme was purified in the same manner as in the case of BTG-1 and a single enzyme was obtained by SDS disc electrophoresis.

c) Preparation of BTG-3

After *Streptoverticillium cinnamoneum* sub s. cinnamoneum IFO 12852 was cultured at 30° C. for 3 days in the same manner as in the case of BTG-1, the system was filtered to give 18.5 liters of culture solution. The activity was 0.5 U/ml.

The enzyme was purified in the same manner as in the case of BTG-1 and a single enzyme was obtained by SDS disc electrophoresis.

Having now generally described this invention, a further understanding can be obtained by reference to certain specific examples which are provided herein for purposes of illustration only and are not intended to be limiting unless otherwise specified.

EXAMPLE 1

After 10 kg of whole soybeans were immersed in water overnight, the beans were ground with a grinder while 20 liters of water were added. Thus, a "GO" slurry was obtained. To the "GO" slurry was added 200 g of a defoaming agent (fatty acid monoglyceride). After water was added to the mixture to make the entire volume 40 liters, the mixture was heated in a cooker. The heating was carried out by elevating the temperature to 100° C. over 5 minutes. The same temperature was maintained for a further 3 minutes. After completion of the heating, the mixture was filtered to give about 45 liters of soy milk.

The soy milk was cooled to 65° C. by allowing the milk to stand at room temperature. After 3 g of glucono-δ-lactone and 350 mg of BTG-1 (specific activity, 2.0 units/mg) were added to the soy milk per 1 liter of the soy milk, the mixture was packed in a molding machine (14 cm × 16 cm × 4 cm) and allowed to stand for an hour. BTG-1 which had been previously inactivated by heating was used in the system for a control.

Each soybean curd was heated to a temperature of 90° C. The temperature was maintained for 10 minutes. After completion of the heating, each soybean curd was withdrawn from the molding machine and exposed to running water for 3 hours. Each soybean curd was cut into a cubic shape having a length of 1.5 cm on each side, 50 g of soybean curd and 100 ml of water were packed in a retort pouch.

The thus prepared sample was treated at 110° C. using a high temperature compression cooking sterilizer manufactured by Hisaka Seisakusho K.K. to show a $F_0$ value of 4.0. In addition, commercially available "KINUGOSHI-TOFU" or silk-strained soybean curd was likewise cut, packed and retort treated as described above.

Each retort-treated soybean curd was subjected to an organoleptic evaluation (texture profile method, 15 panels) using the aforesaid commercially available "KINUGOSHI-TOFU" or silk-strained soybean curd as a control (score 0). The results are shown in Table 6.

From the results, it is clearly noted that the retort-treated soybean curd prepared by acting BTGase thereon had smoothness, softness and good texture comparable to those of the control, whereas the retort-treated soybean curd as a comparison which was prepared without allowing BTGase to act on the soy milk and the retort-treated commercially available "KINUGOSHI-TOFU" or silk-strained soybean curd were hard and dry and showed a texture unfavorable for soybean curds.

EXAMPLE 2

After 600 ml of water was added to 65 g of soy milk powder (manufactured by Nippon Protein Industry K.K., "HIPROTON"), a pan charged with the mixture was heated in a gas oven with stirring. After boiling, the flame was lowered to a definite degree and kept for 3 minutes. Then, the pan was removed from the flame.

While stirring, the mixture was cooled to 70° C., a solution of 2 g of glucono-δ-lactone and 325 mg of BTG-1 (specific activity, 2.0 unit/mg) in 50 ml of water was added to the mixture. For control, BTG-1 which had been previously inactivated by heat was used.

The soy milk described above was immediately packed in a casing tube (manufactured by Kureha Chemical Industry Co., Ltd., folding width of 47 mm). After allowing to stand in a water bath at 55° C. for 30 minutes or at room temperature for an hour, heating was performed in a water bath at 90° C. for 30 minutes. The heated soy milk was withdrawn and cooled in running water. Then, the sample was treated at 110° C. using a high temperature compression cooking sterilizer manufactured by Hisaka Seisakusho K.K. to show a $F_0$ value of 4.0. After the retort treatment, the sample was cooled to room temperature and cut into a size of 3 cm, which was provided for determination of physical properties. For measurement with a rheometer, a spherical plunger having a diameter of 7 mm was used. By setting an elevation velocity on a sample stand at 5 cm/min, breaking strength (g/cm$^2$) and distortion rate (%) of the sample soybean curd were determined. With respect to commercially available "KINUGOSHI-TOFU" (same as used in Example 1), a sample was cut into the same shape as that of the sample provided above for determination of its physical properties.

The results are shown in Table 7. According to the results, the physical properties of the retort-treated soybean curd obtained by allowing BTGase to act thereon are almost identical with those of the commercially available "KINUGOSHI-TOFU" which was not subjected to a retort treatment. However, for the retort-treated soybean curd subjected to no BTGase treatment, the breaking strength increased. That is, it was noted that the sample became solid. Further a comparison of the texture of both showed that the sample obtained by allowing BTGase to act on the milk was soft and smooth, whereas the sample obtained without allowing BTGase to act on the milk was hard and dry.

TABLE 7

| Physical Properties of Retort-Treated Soybean Curd | | |
|---|---|---|
| Sample | Breaking Strength (g/cm$^2$) | Distortion Rate (%) |
| Commercially available "KINUGOSHI-TOFU" (retort-untreated) | 50 | 28 |
| Control (55° C., 30 minutes) | 67 | 25 |
| Control (room temperature, 1 hour) | 70 | 28 |
| BTGase-acted system (55° C., 30 minutes) | 51 | 31 |
| BTGase-acted system (room temperature, 1 hour) | 45 | 31 |

EXAMPLE 3

To 200 g of soybean protein isolate (manufactured by Ajinomoto Inc., "AJIPRON-S2") were added 2000 ml of water and 100 g of soybean oil. After gently dispersing the ingredients, 0.02 g of BTG-1 and 14.5 g of calcium sulfate (dihydrate) were added to the dispersion. The mixture was mixed at 1500 rpm for 15 minutes with a silent cutter. The mixture was molded into a mold having a size of $14 \times 16 \times 4$ cm (length × width × height) and allowed to stand for an hour.

The soybean curd was withdrawn from the mold and exposed to water. The sample was cut into a square of about 3 cm. The soybean curd and a 2-fold amount of water added to the soybean curd were packed in a retort pouch. The sample was treated at 121° C. using a high temperature compression cooking sterilizer manufactured by Hisaka Seisakusho K.K. to show a $F_0$ value of 6.0

After cooling, the resulting soybean curd treated at high temperature under high pressure retains almost the same physical properties as those prior to the retort treatment.

EXAMPLE 4

The retort-treated soybean curd obtained in Example 1 which had been acted upon by BTGase was stored in a thermostat at 25° C. under a relative humidity of 60% as it was. Samples were withdrawn at 1, 3 and 6 months and each sample was subjected to the same organoleptic evaluation as in Example 1. The results are shown in Table 8.

The same procedures were applied to commercially available "KINUGOSHI-TOFU" and long life soybean curd requiring storage in a refrigerator (manufactured by Niigata Milk Industry K.K., "SASAMEYUKI"). Both samples showed marked changes accompanied by putrefaction within one month and were not edible.

From the results, it is clear that stable quality could be retained up to 6 months immediately after preparation of the curd of the present invention.

Having now fully described this invention, it will become apparent to one of ordinary skill in the art that many changes and modifications can be made thereto without departing from the spirit or scope of the invention as set forth herein.

What is claimed as new and desired to be secured by Letters Patent of the United States is:

1. A process for preparing shelf stable soybean curd that is stable for extended periods of time, comprising:
   reacting soy milk with effective amounts of a solidifying agent and a transglutaminase that is not dependent on $Ca^{+2}$ ions and which catalyzes the acyl rearrangement of $\gamma$-carboxyamide in the glutamine residue of a peptide chain at a temperature not higher than 80° C. to prepare a soybean curd;
   packing the thus prepared soybean curd in a heat-resistant container; and
   retorting the packaged soybean curd.

2. The process of claim 1, wherein said solidifying agent is a calcium sulfate hydrate, calcium chloride, brine or a glucono-δ-lactone.

3. The process of claim 1, wherein the concentration of said solidifying agent in the soy milk ranges from 0.1 to 5%.

4. The process of claim 1, wherein said transglutaminase is obtained from a bacterium.

5. The process of claim 4, wherein said bacterium is *Streptoverticillium griseocarneum* IFO 12776, *Streptoverticilliim cinnamoneum* sub s. cinnemoneum IFO 12852 or *Streptoverticillium mobarocense* IFO 13819.

6. The process of claim 1, wherein said packaged soybean curd is retorted at 80° C. to 130° C. for 5 to 120 minutes.

7. The process of claim 6, wherein said retorting is conducted until the soybean curd has an $F_0$ value within the range of 0.2 to 6.

* * * * *

UNITED STATES PATENT AND TRADEMARK OFFICE
CERTIFICATE OF CORRECTION

PATENT NO. : 5,055,310
DATED : October 8, 1991
INVENTOR(S) : Masahiko Nonaka, et. al.

It is certified that error appears in the above-indentified patent and that said Letters Patent is hereby corrected as shown below:

Column 1, line 38, delete "γ-carboxamide", insert --γ-carboxyamide--;
line 56, delete "heat resistant", insert --heat-resistant--.

Column 2, line 3, delete "a", insert --as--.

Column 3, line 17, after "kept", insert --in--.

Column 5, line 26, delete "hydroylamine", insert --hydroxylamine--;
line 55, change "cinnamoneum" (second occurrence) should be in Italics.

Column 6, line 12, after "substrates", insert --and hydroxylamine was examined. None of the BTGases reacted when the synthetic substrates--.

Column 9, lines 9 and 10, change "cinnamoneum" (second occurence) should be Italics.

UNITED STATES PATENT AND TRADEMARK OFFICE
CERTIFICATE OF CORRECTION

PATENT NO. : 5,055,310

DATED : October 8, 1991

INVENTOR(S) : Masahiko Nonaka, et. al.

It is certified that error appears in the above-indentified patent and that said Letters Patent is hereby corrected as shown below:

Column 12, line 32, Claim 5, change "cinnamoneum" (second occurrence) should be Italics.

Signed and Sealed this

Nineteenth Day of October, 1993

Attest:

BRUCE LEHMAN

Attesting Officer     Commissioner of Patents and Trademarks